United States Patent
Zhang et al.

(10) Patent No.: US 9,615,791 B2
(45) Date of Patent: Apr. 11, 2017

(54) WEARABLE DEVICE AND METHOD FOR MANUFACTURING THE SAME

(71) Applicant: Xiaomi Inc., Beijing (CN)

(72) Inventors: Yi Zhang, Beijing (CN); Yongfeng Xia, Beijing (CN); Ningning Li, Beijing (CN); Tao Wang, Beijing (CN); Lian Zhang, Beijing (CN)

(73) Assignee: Xiaomi Inc., Beijing (CN)

( * ) Notice: Subject to any disclaimer, the term of this patent is extended or adjusted under 35 U.S.C. 154(b) by 14 days.

(21) Appl. No.: 14/662,728

(22) Filed: Mar. 19, 2015

(65) Prior Publication Data

US 2016/0021771 A1    Jan. 21, 2016

Related U.S. Application Data

(63) Continuation of application No. PCT/CN2014/091761, filed on Nov. 20, 2014.

(30) Foreign Application Priority Data

Jul. 18, 2014    (CN) .......................... 2014 1 0345261

(51) Int. Cl.
*H05K 5/00*    (2006.01)
*A61B 5/00*    (2006.01)
(Continued)

(52) U.S. Cl.
CPC .............. *A61B 5/681* (2013.01); *G06F 1/163* (2013.01); *H02J 7/0042* (2013.01); *H04B 1/385* (2013.01);
(Continued)

(58) Field of Classification Search
CPC .............. A61B 8/14; A61B 2562/0204; A61G 2505/03
(Continued)

(56) References Cited

U.S. PATENT DOCUMENTS 3,156,922 A * 11/1964 Anderson
6,346,886 B1 * 2/2002 De La Huerga ........ A61J 1/035
340/3.1

(Continued)

FOREIGN PATENT DOCUMENTS

CN          2686229 Y       3/2005
CN        101485559 A       7/2009
(Continued)

OTHER PUBLICATIONS

International Search Report of International Patent Application No. PCT/CN2014/091761, from the State Intellectual Property Office of China (ISA/CN), mailed Apr. 24, 2015 (5 pages).
(Continued)

*Primary Examiner* — Hung S Bui
(74) *Attorney, Agent, or Firm* — Finnegan, Henderson, Farabow, Garrett & Dunner LLP

(57) ABSTRACT

A main body of a wearable device, includes: a front case; a bottom case joined with the front case to form a waterproof cavity; and electronic components disposed in the cavity, the electronic components including a printed circuit board (PCB) having a wireless data transceiving assembly, wherein the bottom case includes two charging contacts formed on an outer side of the bottom case and electrically coupled to the electronic components.

8 Claims, 6 Drawing Sheets

(51) Int. Cl.
| | |
|---|---|
| *H02J 7/00* | (2006.01) |
| *H04B 1/3827* | (2015.01) |
| *H04B 5/00* | (2006.01) |
| *H04B 5/02* | (2006.01) |
| *H04B 1/3888* | (2015.01) |
| *G06F 1/16* | (2006.01) |
| *H04B 1/38* | (2015.01) |

(52) U.S. Cl.
CPC ......... *H04B 1/3888* (2013.01); *H04B 5/0031* (2013.01); *H04B 5/02* (2013.01); *A61B 5/7455* (2013.01); *A61B 2560/045* (2013.01); *A61B 2562/166* (2013.01); *H04B 2001/3894* (2013.01); *H05K 2203/1327* (2013.01)

(58) Field of Classification Search
USPC ........... 361/728–730, 752, 796, 800, 679.01, 361/679.02, 679.21
See application file for complete search history.

(56) References Cited

U.S. PATENT DOCUMENTS

| | | | | |
|---|---|---|---|---|
| D545,220 | S * | 6/2007 | Leung | D10/31 |
| 7,398,151 | B1 * | 7/2008 | Burrell | A63B 24/0062 |
| | | | | 342/357.75 |
| 7,513,019 | B2 * | 4/2009 | Friedman et al. | A44C 5/14 |
| | | | | 24/265 |
| 8,249,547 | B1 | 8/2012 | Fellner | |
| 8,345,414 | B2 * | 1/2013 | Mooring | G04G 17/04 |
| | | | | 248/441.1 |
| 8,610,403 | B2 | 12/2013 | Chen | |
| 8,845,461 | B2 * | 9/2014 | Duke | A63B 69/0071 |
| | | | | 473/447 |
| 2003/0169207 | A1 | 9/2003 | Beigel | |
| 2004/0095732 | A1 * | 5/2004 | Azumi | B60R 16/0239 |
| | | | | 361/752 |
| 2006/0267760 | A1 | 11/2006 | Shecter | |
| 2008/0211677 | A1 | 9/2008 | Shecter | |
| 2011/0126613 | A1 * | 6/2011 | Lin | G01M 3/10 |
| | | | | 73/40 |
| 2011/0254661 | A1 * | 10/2011 | Fawcett | G08B 13/1445 |
| | | | | 340/5.61 |
| 2012/0133328 | A1 | 5/2012 | Chen | |
| 2014/0135631 | A1 | 5/2014 | Brumback et al. | |
| 2014/0156196 | A1 | 6/2014 | Martinez et al. | |
| 2014/0162482 | A1 | 6/2014 | Steuer et al. | |
| 2014/0174958 | A1 | 6/2014 | Martinez et al. | |

FOREIGN PATENT DOCUMENTS

| | | |
|---|---|---|
| CN | 101561336 A | 10/2009 |
| CN | 101673857 A | 3/2010 |
| CN | 203103372 U | 7/2013 |
| CN | 203434229 U | 2/2014 |
| CN | 203555263 U | 4/2014 |
| CN | 103815628 A | 5/2014 |
| CN | 203618896 U | 6/2014 |
| CN | 203632283 U | 6/2014 |
| CN | 103892525 A | 7/2014 |
| CN | 203693601 U | 7/2014 |
| CN | 203709401 U | 7/2014 |
| CN | 104146771 A | 11/2014 |
| CN | 204044676 U | 12/2014 |
| GB | 2 431 858 A | 5/2007 |
| JP | 1993088532 U | 12/1993 |
| JP | 2008106932 A | 5/2008 |
| JP | 2009302795 A | 12/2009 |
| JP | 2011-516174 A | 5/2011 |
| JP | 2013513439 A | 4/2013 |
| JP | 3184761 U | 7/2013 |
| JP | 2013179355 A | 9/2013 |
| JP | 2014078240 A | 5/2014 |
| KR | 10-2010-0050031 | 5/2010 |
| RU | 120502 U1 | 9/2012 |

OTHER PUBLICATIONS

Russian First Office Action of Russian Application No. 2015102202 dated Jun. 1, 2016 (10 pages including translation).

"Fitbit Flex Teardown," http://www.ifixit.com/Guide/history/16050/540738/, Oct. 5, 2013 (9 pages).

* cited by examiner

WEARABLE DEVICE AND METHOD FOR MANUFACTURING THE SAME

CROSS-REFERENCE TO RELATED APPLICATIONS

This application is a Continuation Application of International Application No. PCT/CN2014/091761, filed on Nov. 20, 2014, which is based upon and claims priority to Chinese Patent Application No. CN201410345261.7, filed on Jul. 18, 2014, the entire contents of both of which are incorporated herein by reference.

TECHNICAL FIELD

The present disclosure relates to smart wearable technologies and, more particularly, to a wearable device and a method for manufacturing the same.

BACKGROUND

A wrist band is a decorative article that many people like to wear. With technical advancement, smart wrist bands have been developed, which can perform various functions.

The smart wrist band according to the conventional technology is provided with a built-in sensor to collect the user's health data when the user wears the wrist band. The user may transmit the health data from the wrist band to other devices using a USB (Universal Serial Bus) cable for review and analysis.

SUMMARY

According to a first aspect of the present disclosure, there is provided a main body of a wearable device, comprising: a front case; a bottom case joined with the front case to form a waterproof cavity; and electronic components disposed in the cavity, the electronic components including a printed circuit board (PCB) having a wireless data transceiving assembly, wherein the bottom case includes two charging contacts formed on an outer side of the bottom case and electrically coupled to the electronic components.

According to a second aspect of the present disclosure, there is provided a method for manufacturing a main body of a wearable device, comprising: forming a front case and a bottom case from a polycarbonate material by thermomolding; placing electronic components in a cavity enclosed by the front case and the bottom case; electrically connecting the electronic components with two charging contacts on the bottom case; sealing the cavity to be waterproof; and testing the cavity for waterproofness.

It is to be understood that both the foregoing general description and the following detailed description are exemplary and explanatory only and are not restrictive of the invention, as claimed.

DESCRIPTION OF THE EMBODIMENTS

Embodiments consistent with the present disclosure include a wearable device and a method for manufacturing a wearable device.

Figure 1:
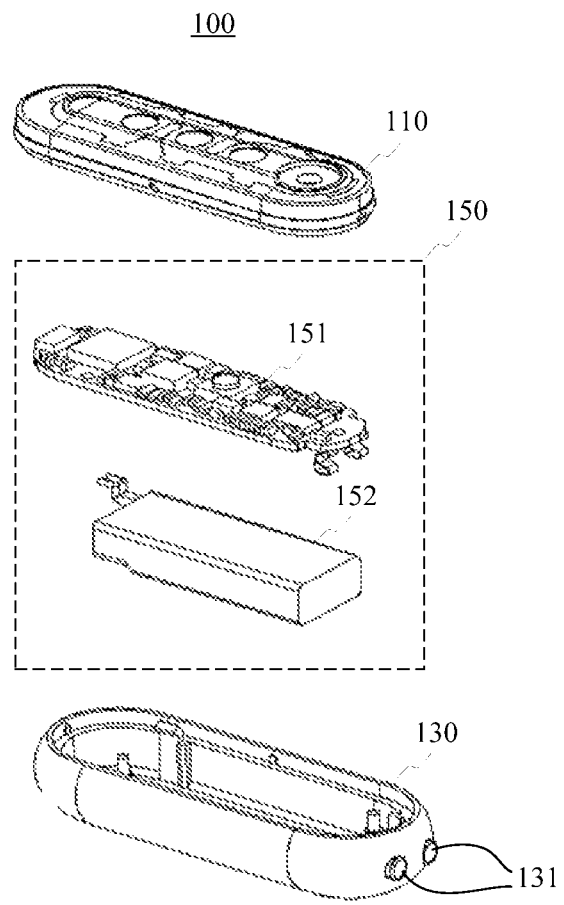
FIG. 1 is an exploded view showing a main body of a wearable device according to one exemplary embodiment.

FIG. 1 is an exploded view showing a main body 100 of a wearable device consistent with embodiments of the disclosure. The main body 100 of the wearable device includes a front case 110, a bottom case 130, and electronic components 150. Consistent with the disclosure, the front case 110 and the bottom case 130 are joined together to form a waterproof cavity, and the electronic components 150 are disposed in the cavity.

The electronic components 150 include a Printed Circuit Board (PCB) 151 and a battery 152, which are electrically connected. The PCB 151 is provided with a wireless data transceiving assembly and at least one sensor.

The bottom case 130 includes two charging contacts 131 formed on an outer side of the bottom case 130 and electrically coupled to the electronic components 150.

Consistent with the present disclosure, since a waterproof cavity containing a wireless data transceiving assembly is provided in a wearable device, a user can wear and use the wearable device in a humid environment or when needing to contact water.

Figure 2:
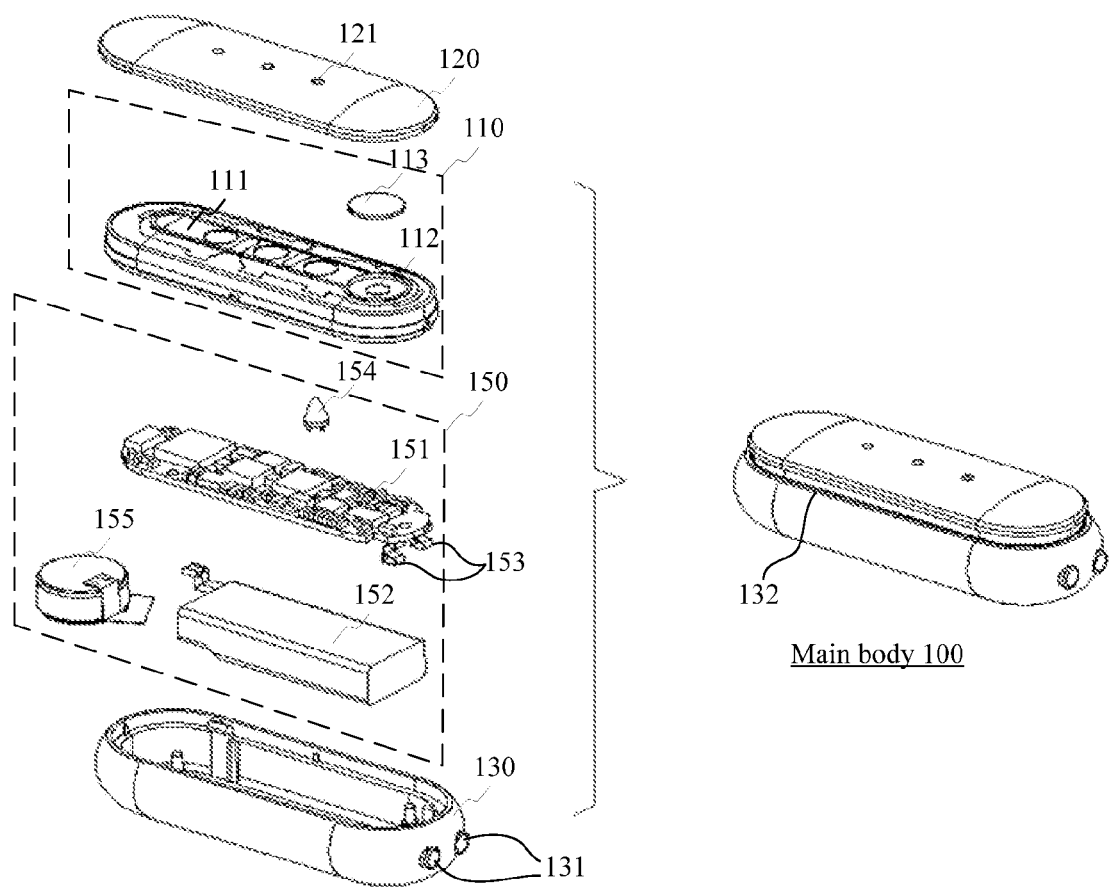
FIG. 2 is an exploded view showing a more detailed structure of the main body shown in FIG. 1.

FIG. 2 is an exploded view showing further details of the main body 100, consistent with embodiments of the disclosure.

As shown in FIG. 2, the electronic components 150 are further provided with two mating contacts 153. The electronic components 150 are electrically coupled to the charging contacts 131 via the mating contacts 153.

The front case 110 includes an outer case surface 111, which is partially or completely transparent. The electronic components 150 further include at least one indicator light 154 disposed on one side of the outer case surface 111. The indicator light 154 is electrically coupled to the PCB 151.

In some embodiments, the main body 100 further includes a front case decorative piece 120, which is attached to an outer side of the outer case surface 111 and is provided with at least one light penetration area 121 corresponding to the indicator light 154. In some embodiments, the indicator light 154 directly faces the light penetration area 121. That is, light emitted by the indicator light 154 passes through the transparent portion of the outer case surface 111, and emits from the main body 100 through the light penetration area 121.

In some embodiments, the front case decorative piece 120 includes a metal decorative piece. Each light penetration area 121 includes several evenly-arranged micro-apertures that extend through the metal decorative piece from a lower surface to an upper surface thereof. The micro-apertures include light penetration fillers provided therein. The light penetration fillers may include a UV (Ultraviolet Rays) glue. For example, the light penetration area 121 is a round area with a diameter of 2.5 mm, in which there are provided 170 micro-apertures each having a diameter of 0.07 mm.

In some embodiments, the front case decorative piece 120 includes laser engraved heat-melting adhesive patterns formed on a surface of the front case decorative piece 120 that faces the front case 110. The front case decorative piece 120 is glued to an outer surface of the front case 110 by the heat-melting adhesive patterns.

In some embodiments, a through hole 112 for testing waterproofness is formed on the front case 110. A waterproof seal 113 covers the through hole 112.

In some embodiments, when the front case 110 is jointed with the bottom case 130, the outer case surface 111 of the front case 110 projects beyond a jointing edge 132 of the bottom case 130.

In some embodiments, the electronic components 150 include a vibration motor 155, which is electrically coupled to the PCB 151 and the battery 152.

Figure 3:
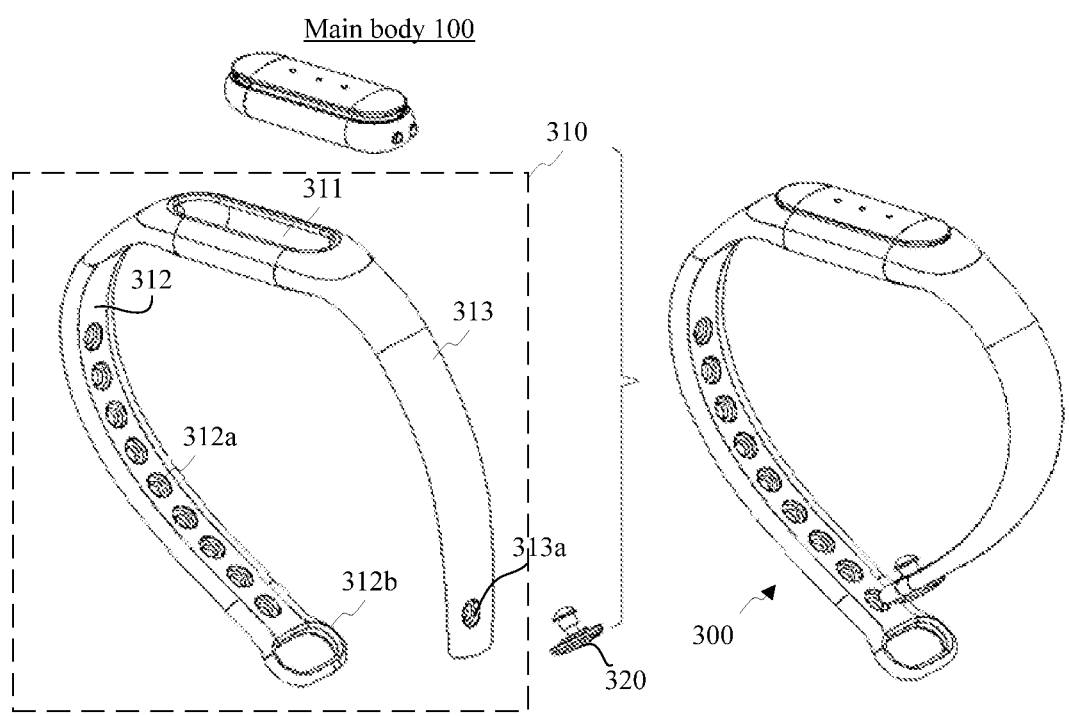
FIG. 3 is a schematic view showing a wearable device according to an exemplary embodiment.

FIG. 3 is a schematic view showing an exemplary wearable device consistent with embodiments of the disclosure. The wearable device shown in FIG. 3 includes the main body 100 and a flexible wrist band 300 for accommodating the main body 100.

The flexible wrist band 300 includes a wrist band main body 310 and a wrist buckle 320. The wrist band main body 310 has a center portion, which is provided with an accommodating groove 311 configured to receive the main body 100. The wrist band main body 310 further includes a first wrist band part 312 and a second wrist band part 313 extending respectively from both ends of the center portion. The first wrist band part 312 includes at least one fixed hole 312a. A terminal end of the first wrist band part 312 includes an annular structure 312b, configured to allow the second wrist band part 313 to pass through. The second wrist band part 313 includes a buckle hole 313a.

The wrist band buckle 320 can be inserted into the buckle hole 313a. When a terminal end of the second wrist band part 313 passes through the annular structure 312b, the wrist band buckle 320 can be inserted into the fixed hole 312a of the first wrist band part 312 to secure the first wrist band part 312 to the second wrist band part 313.

Consistent with the present disclosure, since the main body is received in the accommodating groove, the charging contacts are prevented from being exposed. Further, the wearable device can be worn at a desired body portion via the wrist band main body.

Figure 4:
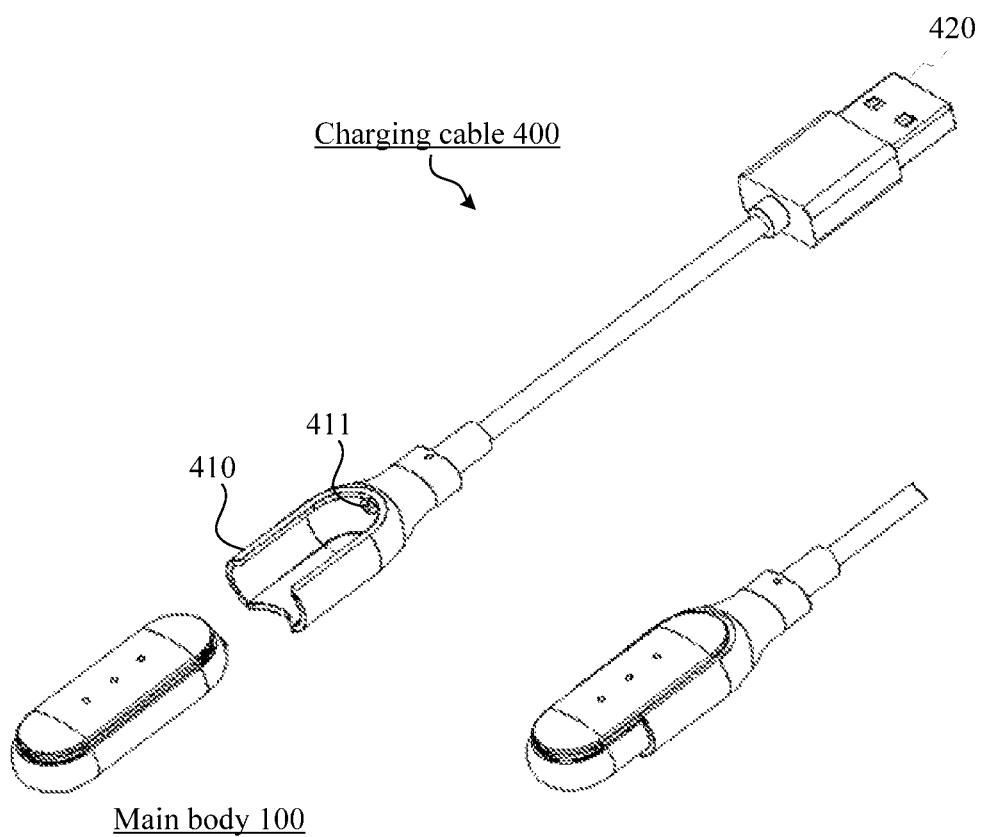
FIG. 4 is a schematic view showing a wearable device according to another exemplary embodiment.

FIG. 4 is a schematic view showing another exemplary wearable device consistent with embodiments of the disclosure. The wearable device shown in FIG. 4 includes the main body 100 and a charging cable 400 for charging the main body 100.

The charging cable 400 includes a main body accommodating end 410 and a charging end 420. The main body accommodating end 410 includes a semi-cavity for accommodating the main body 100. Two charging terminals 411 are formed on an inner surface of the semi-cavity and configured to electrically contact the two charging contacts 131 of the main body 100 when the main body 100 is inserted into the semi-cavity. The two charging terminals 411 of the main body accommodating end 410 are electrically coupled to the charging end 420.

The charging end 420 includes at least one of a USB interface, a Mini USB interface, a Micro USB interface, a 30-pin interface, or a power adapter. In the example shown in FIG. 4, the charging end 420 includes a USB interface. Consistent with embodiments of the present disclosure, charging cables having different charging ends can be provided for the main body 100 so that the main body 100 can be charged using different ports.

The exemplary wearable devices shown in FIGS. 3 and 4 include the main body 100 described above in connection with FIGS. 1 and 2. A wearable device consistent with the present disclosure may alternatively include another main body consistent with the present disclosure, instead of the main body 100.

Figure 5:
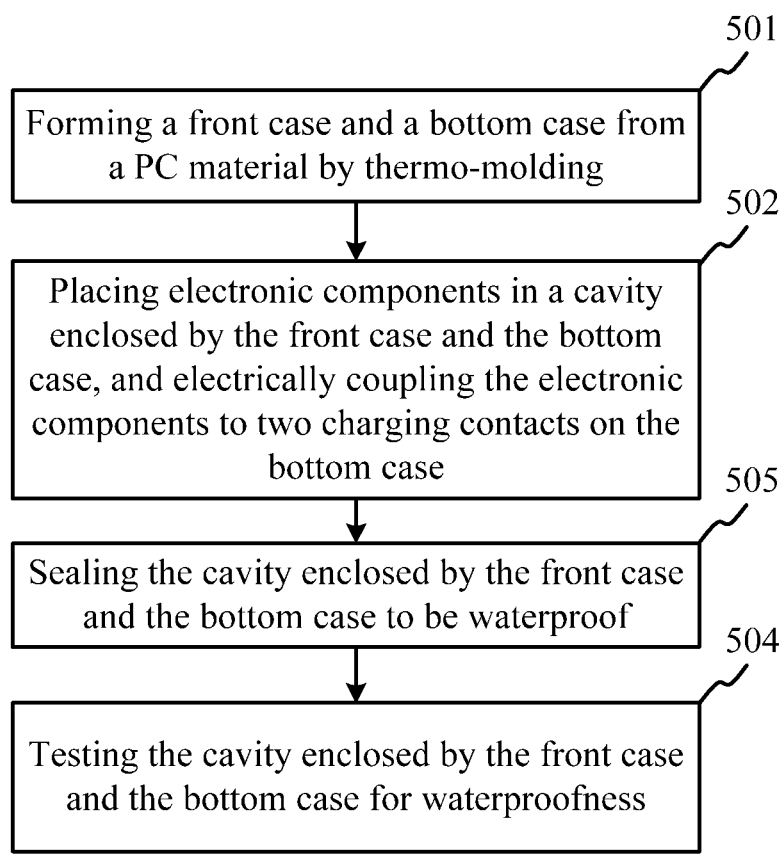
FIG. 5 is a flow chart of a method for manufacturing the main body of the wearable device according to an exemplary embodiment.

FIG. 5 is a flow chart of an exemplary method for manufacturing a main body of wearable device, such as the main body 100 shown in FIGS. 1 and 2, consistent with embodiments of the present disclosure. As shown in FIG. 5, at 501, a front case and a bottom case are formed from a polycarbonate (PC) material by thermo-molding. At 502, electronic components are placed in a cavity enclosed by the front case and the bottom case, and the electronic components are electrically coupled to two charging contacts on the bottom case. At 503, the cavity enclosed by the front case and the bottom case is sealed to be waterproof. At 504, the cavity enclosed by the front case and the bottom case is tested for waterproofness.

Figure 6:
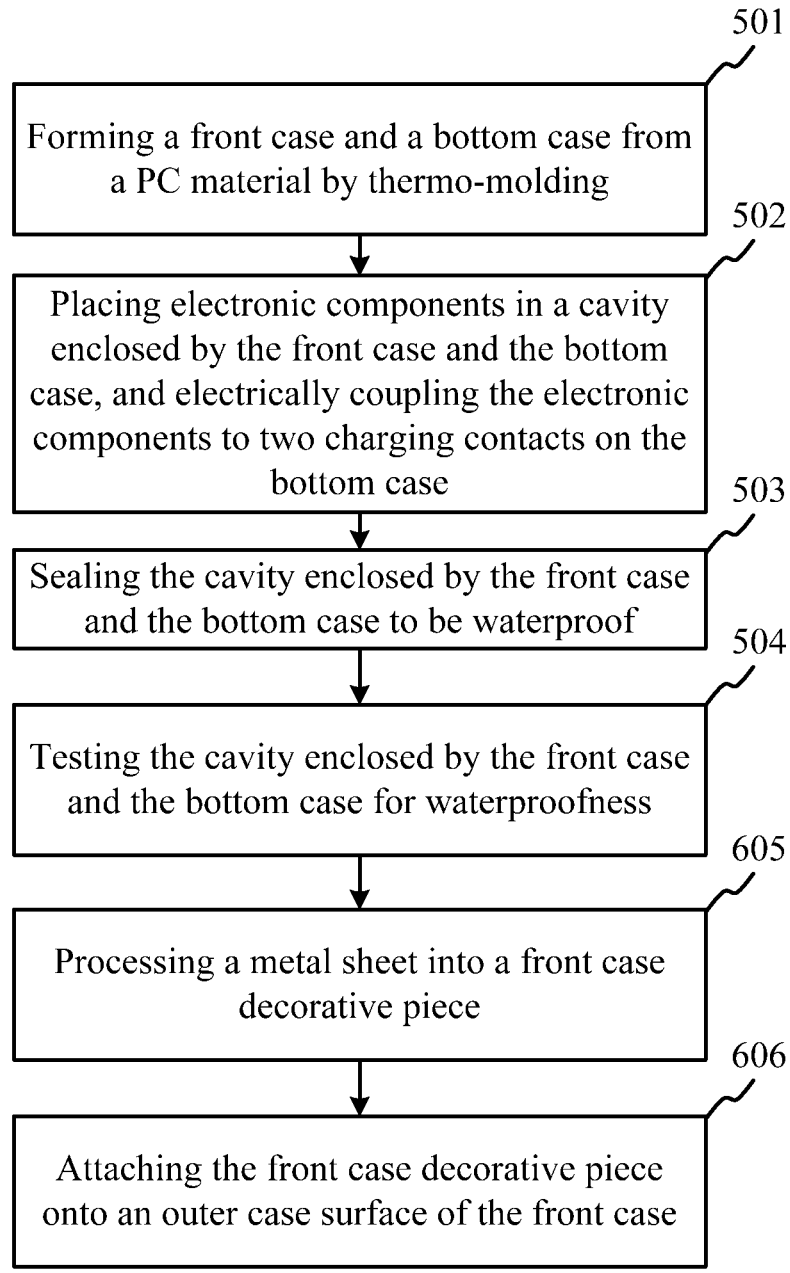
FIG. 6 is a flow chart of a method for manufacturing the main body of the wearable device according to another exemplary embodiment.

FIG. 6 is a flow chart of another exemplary method for manufacturing a main body of a wearable device, such as the main body 100 shown in FIGS. 1 and 2, consistent with embodiments of the present disclosure. The method shown in FIG. 6 is similar to the method shown in FIG. 5, except that the method shown in FIG. 6 includes two additional steps 605 and 606. As shown in FIG. 6, at 605, a metal sheet is processed into a front case decorative piece. At 606, the front case decorative piece is attached onto an outer case surface of the front case.

In some embodiments, forming the front case (501 in FIGS. 5 and 6) includes forming a front case with an outer case surface having a shape of a rectangle with rounded corners and a case edge extending along a direction perpendicular to the outer case surface from an edge of the outer case surface. The outer case surface is transparent, such as partially or completely transparent.

In some embodiments, placing the electronic components in the cavity (502 in FIGS. 5 and 6) includes placing electronic components containing a PCB, a power motor, a battery, an indicator, a wireless data transceiving assembly, and at least one sensor. Electrically coupling the electronic components to the two charging contacts on the bottom case (502 in FIGS. 5 and 6) includes electrically coupling two mating contacts of the electronic components to the two charging contacts on the bottom case.

In some embodiments, sealing the cavity (503 in FIGS. 5 and 6) includes sealing the cavity by, for example, a sealing method using an O-shaped ring.

In some embodiments, testing the cavity for waterproofness (504 in FIGS. 5 and 6) includes forming a through hole on the front case; testing the cavity for waterproofness by pressurizing a gas through the through hole into the cavity, i.e., determining whether the cavity passes the waterproof test by checking a pressure loss; and sealing the through hole using a waterproof sealing paste when the cavity passes the waterproof test.

In some embodiments, processing the metal sheet (605 in FIG. 6) includes processing a metal sheet, such as an aluminum alloy, into a rectangular sheet with rounded corners by press molding; polishing, sandblasting, and oxidizing an outer surface of the rectangular sheet with rounded corners; performing high-light polishing on side edges of the rectangular sheet with rounded corners, and oxidizing the rectangular sheet with rounded corners for a second time after the high-light polishing; milling a light penetration area having a lower portion directly facing an indicator light positioned under a transparent area of the outer case surface, of the rectangular sheet with rounded corners; drilling a predetermined number of micro-apertures in the light penetration area using, for example, a laser; injecting a UV curable glue into the micro-apertures; and irradiating a UV light on the micro-apertures to cure the UV curable glue in the micro-apertures.

Consistent with embodiments of the present disclosure, since the light penetration area is milled, light transmittance of the rectangular sheet with rounded corners is increased. As a result, the indicator light can operate with a lower brightness and thus energy consumption by the indicator light can be reduced.

In some embodiments, attaching the front case decorative piece onto the outer case surface of the front case (606 in FIG. 6) includes laser engraving heat-melting adhesive patterns on a surface of the front case decorative piece facing the front case; and connecting the front case decorative piece to the outer case face of the front case through the heat-melting adhesive patterns.

Consistent with embodiments of the disclosure, a bonding strength between the front case decorative piece and the front case is increased by using the laser engraved heat-melting adhesive patterns.

A person skilled in the art may anticipate other solutions after consideration of the above description and implementation of the present disclosure. The present disclosure intends to cover any variation, usage, or modification which follow a general principle of the present disclosure and include common knowledge or usual technical means in the art.

It will be appreciated that the above embodiments are exemplary and the present disclosure is not limited thereto, and that various modifications and changes can be made without departing from the scope thereof. It is intended that the scope of the invention only be limited by the appended claims.

What is claimed is:

1. A main body of a wearable device, comprising:
    a front case including an outer case surface that is partially or completely transparent;
    a bottom case joined with the front case to form a waterproof cavity;
    electronic components disposed in the cavity, the electronic components including:
        a printed circuit board (PCB) having a wireless data transceiving assembly; and
        an indicator light electrically coupled to the PCB, the indicator light being disposed proximate to an inner side of the outer case surface facing the cavity; and
    a front case decorative piece attached to an outer side of the outer case surface, the front case decorative piece including a light penetration area corresponding to the indicator light,
    wherein the bottom case includes two charging contacts formed on an outer side of the bottom case and electrically coupled to the electronic components.

2. The main body according to claim 1, wherein:
    the front case decorative piece includes a metal decorative piece,
    the light penetration area includes a plurality of micro-apertures that extend through the metal decorative piece, and
    the front case decorative piece further includes light penetration fillers filled in the micro-apertures.

3. The main body according to claim 1, further comprising:
    laser engraved heat-melting adhesive patterns gluing the front case decorative piece to an outer surface of the front case.

4. The main body according to claim 1, wherein the front case includes a through hole for testing waterproofness, the through hole being sealed with a waterproof sealing paste.

5. The main body according to claim 1, wherein the outer case surface projects beyond a jointing edge of the bottom case.

6. The main body according to claim 1, wherein the electronic components further include a vibration motor electrically coupled to the PCB.

7. A wearable device, comprising:
    a main body according to claim 1; and
    a flexible wrist band including:
        a wrist band main body including:
            a center portion having an accommodating groove configured to receive the main body;
            a first wrist band part extending from one end of the center portion, the first wrist band part including:
                a fixed hole; and
                an annular structure provided at a terminal end of the first wrist band part;
            a second wrist band part extending from another end of the center portion, the second wrist band part including a buckle hole and being configured to pass through the annular structure; and
        a wrist band buckle configured to be inserted into the buckle hole and into the fixed hole, to secure the first wrist band part to the second wrist band part when a terminal end of the second wrist band part passes through the annular structure.

8. A wearable device, comprising:
    a main body according to claim 1; and
    a charging cable for charging the main body, the charging cable including:
        a main body accommodating end including:
            a semi-cavity configured to receive the main body; and
            two charging terminals formed on an inner surface of the semi-cavity and configured to electrically contact two mating contacts of the main body when the main body is inserted into the semi-cavity; and
        a charging end electrically coupled to the two charging terminals, the charging end including one of a Universal Serial Bus (USB) interface, a Mini USB interface, a Micro USB interface, a 30-pin interface, or a power adapter.

* * * * *